United States Patent
Chopdekar et al.

(10) Patent No.: US 7,683,042 B1
(45) Date of Patent: *Mar. 23, 2010

(54) STABILIZED HALIDE-FREE GLUCOSAMINE BASE AND METHOD OF PREPARATION

(75) Inventors: Vilas M. Chopdekar, Edison, NJ (US); Sham N. Redkar, Bound Brook, NJ (US)

(73) Assignee: JFC Technologies, LLC, Bound Brook, NJ (US)

( * ) Notice: Subject to any disclaimer, the term of this patent is extended or adjusted under 35 U.S.C. 154(b) by 801 days.

This patent is subject to a terminal disclaimer.

(21) Appl. No.: 11/223,688

(22) Filed: Sep. 9, 2005

Related U.S. Application Data

(60) Provisional application No. 60/611,180, filed on Sep. 17, 2004.

(51) Int. Cl.
*A61K 31/70* (2006.01)
*C07H 5/04* (2006.01)

(52) U.S. Cl. .................. 514/62; 536/55.2; 536/55.3

(58) Field of Classification Search .............. None
See application file for complete search history.

(56) References Cited

U.S. PATENT DOCUMENTS

| | | | | |
|---|---|---|---|---|
| 3,683,076 | A | 8/1972 | Rovati | 424/180 |
| 4,642,340 | A | 2/1987 | Senin et al. | 536/55.2 |
| 5,843,923 | A | 12/1998 | Schleck et al. | 514/62 |
| 5,902,801 | A | 5/1999 | Schleck et al. | 514/62 |
| 6,346,519 | B1 * | 2/2002 | Petrus | 514/62 |
| 6,472,380 | B1 | 10/2002 | Schleck et al. | 514/62 |
| 6,486,307 | B1 | 11/2002 | Gandhi et al. | 536/20 |
| 6,723,363 | B2 * | 4/2004 | Ziegler et al. | 426/302 |
| 7,388,000 | B1 * | 6/2008 | Redkar et al. | 514/62 |
| 7,388,001 | B1 * | 6/2008 | Chopdekar et al. | 514/62 |
| 2003/0148998 | A1 | 8/2003 | Fan et al. | 514/62 |
| 2004/0030121 | A1 | 2/2004 | Mukhopadhyay et al. | 536/55.2 |
| 2004/0077055 | A1 | 4/2004 | Fosdick et al. | 435/85 |
| 2004/0091976 | A1 | 5/2004 | Deng et al. | 435/84 |
| 2005/0014720 | A1 | 1/2005 | Vila Pahi et al. | 514/62 |
| 2005/0148545 | A1 | 7/2005 | Fosdick et al. | 514/62 |
| 2005/0148546 | A1 | 7/2005 | Grund et al. | 514/62 |

FOREIGN PATENT DOCUMENTS

| | | |
|---|---|---|
| EP | 0 214 642 A2 | 3/1987 |
| WO | WO8000659 * | 4/1980 |
| WO | WO2004003175 * | 1/2004 |

OTHER PUBLICATIONS

PurePharm Inc. Glucosamine: A Glycobiology Primer. 2003. Accessed from http://www.ultimateglucosamine.com/consumers/glycobiology.shtml on Aug. 26, 2008, pp. 1-16.*

* cited by examiner

*Primary Examiner*—David J Blanchard
*Assistant Examiner*—Rachael E Welter
(74) *Attorney, Agent, or Firm*—Jack Matalon

(57) ABSTRACT

A stabilized glucosamine base composition comprising a glucosamine base having a purity level of at least 99.0 wt. % and a maximum halide content of about 0.01 wt. % coated with at least one pharmaceutically acceptable polymer comprising a water-soluble, water-immiscible and/or water-swellable homopolymer and/or copolymer. The resultant coated glucosamine base composition will be stable at ambient temperatures and upon exposure to the atmosphere. Suitable polymers include carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

15 Claims, No Drawings

STABILIZED HALIDE-FREE GLUCOSAMINE BASE AND METHOD OF PREPARATION

CROSS-REFERENCE TO RELATED APPLICATION

This application claims the benefit of Provisional Application Ser. No. 60/611,180 filed Sep. 17, 2004.

FIELD OF THE INVENTION

The invention relates to a stabilized halide-free glucosamine base and a method for preparing such stabilized halide-free glucosamine base.

BACKGROUND OF THE INVENTION

Glucosamine is a well-known amino monosaccharide found in chitin, glycoproteins and glycosaminoglycans. Glucosamine is widely used for the treatment of rheumatic fever, arthritic and arthosic complaints, in the acute as well as chronic forms, as well as in the treatment of pathological conditions originating from metabolic disorders of the osteoarticular tissue. Although products in the marketplace are labeled as, or referred to as, "glucosamine" or "stabilized glucosamine", they are misnomers, since such products consist of glucosamine hydrochloride or unreacted mixtures of glucosamine hydrochloride and a salt such as potassium or sodium sulfate.

Mixed salts of glucosamine hydrochloride and alkaline or earth alkaline metal sulfates such as potassium sulfate, and sodium sulfate are well known. Such mixed salts are used rather than glucosamine sulfate alone since the latter is unstable in view of its highly hygroscopic nature and the facility with which its amino group oxidizes if not completely saltified, see, e.g., U.S. Pat. No. 4,642,340 and U.S. Pat. No. 3,683,076 which disclose mixtures of glucosamine sulfate and glucosamine hydroiodide.

Free glucosamine base may be prepared by the method recited in *Chem. Ber.,* volume 75, page 1274. Such method involves the treatment of glucosamine hydrochloride with an ethanolic solution of a tertiary base such as triethylamine. Triethylamine hydrochloride is filtered off and the free glucosamine is then recovered from the reaction mixture. However, triethylamine is a toxic material even in small quantities and the yield of the free glucosamine base is quite low. Moreover, the free glucosamine base still contains residual chloride.

In EP 0 214 642, free glucosamine base containing residual chloride is converted to a mixed salt of glucosamine sulfate and potassium chloride by dissolving the glucosamine base in water, adding a stoichiometric quantity of concentrated sulfuric acid to form a solution of glucosamine sulfate in water and dissolving a stoichiometric amount of potassium chloride in the solution. The mixed salt is precipitated from the solution by addition of a precipitant such as isopropanol, stirring the mixture for about 14 hours to complete the precipitation, cooling the reaction mass to 0° C. and recovering the precipitated salt by filtration. This process results in low yields.

Free glucosamine base may also be prepared by microbial fermentation. For example, see US Published Patent Application Publication Nos. 2004/0091976 A1, 2004/0077055 A1 and 2003/0148998 A1. It is known to prepare glucosamine by deacetylation of n-acetyl-glucosamine, see US Published Patent Application Publication No. 2005/0145846 A1. Glucosamine hydrochloride may also be prepared by the process disclosed in U.S. Pat. No. 6,486,307; the process involves the grinding of chitin to a very fine size, followed by digestion with concentrated hydrochloric acid. The crude glucosamine hydrochloride is then decolorized with activated charcoal and assayed by pH titration with a base.

In US Published Patent Application 2004/0030121, free glucosamine base containing residual chloride is converted to a mixed salt of glucosamine sulfate and potassium chloride by dissolving the glucosamine base in water, adding a stoichiometric quantity of concentrated sulfuric acid to form a solution of glucosamine sulfate in water and dissolving a stoichiometric amount of potassium chloride in the solution. The mixed salt is precipitated from the solution by addition of a precipitant such as isopropanol, stirring the mixture for about 14 hours to complete the precipitation, cooling the reaction mass to 0° C. and recovering the precipitated salt by filtration. This process results in low yields.

Regardless of the source of the glucosamine, it is commercially available only in the form of a halide salt, usually the hydrochloride, since the glucosamine free base can only be isolated from aqueous reaction mixtures in the form of its salt. Furthermore, free glucosamine base is unstable at ambient temperatures and is quite hygroscopic and it is therefore converted to a halide salt before being marketed.

In co-pending patent application Ser. No. 11/223,336 filed Sep. 9, 2005 (corresponding to provisional application No. 611,709 filed Sep. 17, 2004), the disclosure of which is incorporated herein in its entirety by reference, a process is disclosed for converting a glucosamine halide into a halide-free glucosamine base. The resultant halide-free glucosamine base may then be used as is for those medicinal purposes in which the presence of a salt such as sodium or potassium chloride, sodium or potassium sulfate, sodium or potassium iodide, etc. is undesirable. The halide-free glucosamine base may also be employed to prepare a wide variety of useful derivatives such as glucosamine salts, e.g., glucosamine sulfate, glucosamine phosphate, glucosamine salts of α-hydroxy acids (e.g., lactic acid, citric acid, etc.), n-acetylglucosamine, glucosamine salts of drugs having acidic functionalities, etc., wherein such derivatives do not contain any objectionable cations such as sodium or potassium.

The halide-free glucosamine base prepared by the process disclosed in the above-identified co-pending provisional application is unstable—it is quite hygroscopic and will readily decompose when exposed to ambient temperatures and/or the atmosphere. Therefore, the halide-free glucosamine base must be kept refrigerated in a closed container, thereby limiting the usefulness of the product. It would be most desirable if a method could be found for stabilizing the halide-free glucosamine base without having any adverse affect on the physical and chemical properties on the halide-free glucosamine base such that the halide-free glucosamine base could be exposed to the atmosphere and stored at ambient temperatures without decomposition occurring.

DETAILS OF THE INVENTION

The invention relates to a stabilized halide-free glucosamine base and a method for preparing such stabilized halide-free glucosamine base. The method for preparing the halide-free glucosamine base as disclosed in the above-identified co-pending patent application, involves the following steps:

(a) a glucosamine halide (e.g., glucosamine hydrochloride, glucosamine hydroiodide, etc.) is reacted with a lithium base in the presence of a $C_1$-$C_4$ alcohol to thereby generate a $C_1$-$C_4$ alcohol solution of a lithium halide and an insoluble halide-free glucosamine base; and (b) the insoluble halide-free glucosamine base is separated from the $C_1$-$C_4$ alcohol solution of the lithium halide salt.

For maximum yields, the reaction should be carried out at a temperature of about 15 to about 35° C.; conveniently, the reaction may be carried out at ambient temperatures.

The $C_1$-$C_4$ alcohol may be, e.g., methanol, ethanol (preferably anhydrous), isopropanol, etc.; the preferred alcohol comprises methanol. The lithium base may be anhydrous lithium hydroxide, lithium hydroxide monohydrate, lithium methoxide, lithium ethoxide or lithium isopropoxide. The preferred lithium base comprises anhydrous lithium hydroxide. It has been found that the presence of water in the reaction mixture reduces the yield of the halide-free glucosamine base. Accordingly, it is preferred that the reaction be carried out under anhydrous conditions. In general, the lithium base is employed in an amount of about 1.0 to about 1.2 moles per mole of halide present in the glucosamine halide salt. Excess lithium base is unnecessarily wasteful and will reduce the yield of the halide-free glucosamine base. Typically, the alcohol is employed in an amount of about 1 to about 10 parts, preferably 3 to 6 parts, per part of lithium base.

After allowing the reaction to proceed (preferably with agitation) for about 5 minutes to about 2 hours, the solid halide-free glucosamine base is filtered off from the resultant alcohol solution of the lithium halide and washed with additional alcohol. The halide-free glucosamine base may then be dried under vacuum at a temperature of about 15 to about 30° C. The yield typically ranges from about 85 to about 90%. The halide-free glucosamine base is quite pure. It will have a purity level of at least about 99 wt. % and the halide content will be about 0.01 wt. % or less, e.g., 100 ppm or less and very often, the halide content will be less than 50 ppm. Based upon the residual halide content of the halide-free glucosamine base, the lithium residue in the glucosamine base will generally be a maximum of 20 ppm and very often, the lithium residue content will be less than 10 ppm.

The halide-free glucosamine base may be readily stabilized by coating the base with a pharmaceutically acceptable polymer, i.e., a water-soluble, water-dispersible and/or or a water-swellable homopolymer and/or copolymer. Preferably, the pharmaceutically acceptable polymer will be water-soluble. In general, the polymer will be employed in an amount of about 2 to about 70, preferably 20 to 50, parts by weight of the polymer per part of the base. Nonlimiting examples of commercially available pharmaceutically acceptable homopolymers and copolymers suitable for stabilizing the halide-free glucosamine base include the following: carboxypolymethylene homopolymers and copolymers, i.e., vinyl polymers having active carboxyl groups such as high molecular weight homopolymers of acrylic acid crosslinked with allylsucrose or allylpentaerythritol and copolymers of acrylic acid modified by long chain ($C_{10}$-$C_{30}$) alkyl acrylates and crosslinked with allylpentaerythritol—such polymers are commercially available and are marketed as Carbopol® polymers; polyethylene glycol homopolymers and copolymers (e.g., polyethylene-co-lactic acid copolymers), particularly polyethylene glycol polymers having molecular weights in the range of about 2,000 to about 20,000, preferably 4,000 to 18,000; polypropylene glycol homopolymers and copolymers, especially polypropylene glycol homopolymers having molecular weights of about 800 to about 18,000; ethylcellulose; povidone homopolymers, i.e., synthetic water-soluble homopolymers of N-vinyl-pyrrolidone, especially those having a molecular weight of about 2,500 to about 10,000; copovidone, i.e. synthetic random copolymers of N-vinylpyrrolidone and vinyl acetate in a 60:40 ratio; polyacrylic acid homopolymers and copolymers; polyacrylamide homopolymers and copolymers; polysaccharides; etc.

The choice of particular homopolymers and/or copolymers for coating, i.e., stabilizing, the halide-free glucosamine base is not critical so long as the polymers are pharmaceutically acceptable, have the capability of coating, i.e., stabilizing, the halide-free glucosamine base without any adverse chemical reaction occurring between the selected polymers and the halide-free glucosamine base and the resultant coated halide-free glucosamine base compositions are stable, i.e., they will not undergo decomposition when exposed to ambient temperatures and/or the atmosphere.

The method for stabilizing the halide-free glucosamine base is straightforward: The halide-free glucosamine base is dissolved in water (preferably purified water) with agitation for about five to about sixty minutes; in general, about 5 to about 30, preferably 15 to 20 parts of water is employed per part of halide-free glucosamine base. Although lesser amounts of water may be used, the solution may be too viscous to be properly mixed after the pharmaceutically acceptable homopolymer and/or copolymer has been added in the next step. Excessive amounts of water are undesirable since it may be expensive and time-consuming to recover the polymer-coated halide-free glucosamine base from a large volume of the reaction mixture.

The desired pharmaceutically acceptable polymer is added, preferably in increments, with stirring, to the aqueous halide-free glucosamine solution. This step will generally take about 5 to about 15 minutes and is preferably conducted at a temperature of about 15 to about 40° C. After all increments of the selected polymer have been added, stirring is continued for an additional 5 to 60 minutes. As mentioned above, the polymer is employed in an amount of about 2 to about 70, preferably 20 to 50, parts by weight per part of the halide-free glucosamine base.

The last step is the recovery of the polymer-coated, i.e., stabilized, halide-free glucosamine base from the reaction mixture. The stabilized halide-free glucosamine base is recovered from the reaction mixture by freeze-drying or by adding a water-miscible solvent, e.g., acetone, to the reaction mixture to cause the stabilized halide-free glucosamine base to precipitate out from the reaction mixture. The precipitate is then recovered by conventional filtration methods and the product may then be dried, e.g., by conventional methods such as a stream of nitrogen, a vacuum oven at 30-50° C. for 1-10 hours or more, etc. Of course, the choice of stabilizing polymer and water-miscible solvent should be such that the polymer will not dissolve in, or otherwise react with, the solvent.

The stabilized halide-free glucosamine base is preferably recovered by removal of water from the reaction mixture by freeze-drying, a well-known technique for removing water from compositions. Although freeze-drying is a time-consuming process, (a reaction mixture containing one liter of water will typically require 30-36 hours to remove about 97% of the water), it is preferred since the formation of decomposition products resulting from heating the reaction mixture or adding solvents to the reaction mixture can be avoided.

The freeze-drying process will generally be carried out at a reduced pressure and reduced temperature, e.g., a pressure of not greater than 500 milliTorre, preferably 300 to 100 milliTorre and at a temperature of about −60 to about −20° C., preferably −50 to −40° C. The endpoint of completion of the freeze-drying process may be determined by condensing and measuring the quantity of water removed during the freeze-drying process. The time required for completion of the freeze-drying process will vary depending on factors such as pressure, temperature, quantity of reaction mixture to be freeze-dried, level of water to be tolerated in the stabilized halide-free glucosamine base, the thickness and surface area of the reaction mixture in the trays of the freeze-drying equipment, etc.

If the stabilized halide-free glucosamine base is to be recovered by precipitation from the reaction mixture by addition of a water-miscible solvent such as acetone to the reaction mixture, generally about 2 to about 10 parts of solvent per part of reaction mixture will be required.

After the stabilized halide-free glucosamine base has been recovered from the reaction mixture, it may be dried by conventional techniques, e.g., a stream of nitrogen, vacuum oven at a temperature of about 20 to about 50° C., etc.

Not only are the glucosamine compositions of the invention free of halide, but they are also free of the salts that are present in currently available "glucosamine" compositions. Thus a patient who cannot or who does not wish to ingest salts when ingesting currently available "glucosamine" may now be able to ingest true glucosamine containing neither extraneous cations nor halides.

It should also be noted that the stabilization of the halide-free glucosamine base compositions of the invention offers an additional advantage to the patients who ingest such compositions. The stabilized, i.e., polymer-coated, versions of the halide-free glucosamine base compositions provide extended release properties, i.e., the glucosamine base is released within the patient over an extended period of time, thereby minimizing gastric intolerance problems and also resulting in a reduction of the dosage that is required to be ingested over a particular time frame.

The following nonlimiting examples shall serve to illustrate the preferred embodiments of the invention. Unless otherwise indicated, all parts and percentages are on a weight basis.

EXAMPLE 1

Ten grams of a halide-free glucosamine base (solid, white material) were physically mixed with 5 grams of Carbopol® polymer in a bottle by shaking the solids together for about five minutes. The resultant physical mixture was then allowed to remain in an open dish at ambient temperatures. It was noted that after three months in the open dish, there was no significant color change, indicating that physical mixing of the polymer with the halide-free glucosamine base satisfactorily stabilized the base.

EXAMPLE 2

Ten grams of a halide-free glucosamine base were dissolved in 100 g of purified water. Thereafter, 2 g of ethylcellulose were slurried in the aqueous solution and the slurry was mixed for a few minutes. The water was then removed by freeze-drying at a pressure of about 200 milliTorre and a temperature of about –45° C. The yield was 11.5 g. Some of the material was placed in a capped-bottle and the bottle was stored at ambient temperature. The material in the bottle did not change color over a six-month period. Another portion of the material was placed in an open dish and exposed to air; after a period of a few days, the material in the dish developed a slight yellow color.

EXAMPLE 3

Two grams of polyethylene glycol homopolymer having a molecular weight of 4,000 were placed in a flask and 150 g methylene chloride were added to the flask which was then stirred for several minutes to obtain complete dissolution of the homopolymer. Thereafter, 10 g of halide-free glucosamine base were charged to the flask and the contents were stirred for one hour at ambient temperature. The methylene chloride was removed by means of a rotary evaporator and 11.4 g of a white solid were obtained. The white solid was stored in a capped-bottle at ambient temperature and developed no color change over a three-month period.

What is claimed is:

1. A composition comprising glucosamine base coated with a pharmaceutically acceptable polymer, said glucosamine base having a purity level of at least 99.0 wt. % and a maximum halide content of about 0.01 wt. %.

2. The composition of claim 1 wherein the polymer comprises a water-soluble, water-dispersible and/or a water-swellable homopolymer and/or copolymer.

3. The composition of claim 1 wherein the polymer is present in the composition in an amount of about 2 to about 70 parts by weight, per part of the base.

4. The composition of claim 1 wherein the polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

5. The composition of claim 4 wherein the polymer comprises a carboxypolymethylene homopolymer or copolymer.

6. The composition of claim 4 wherein the polymer comprises a polyethylene glycol homopolymer or copolymer having a molecular weight of about 2,000 to about 20,000.

7. The composition of claim 4 wherein the polymer comprises ethylcellulose.

8. A method for preparing a stabilized glucosamine base composition comprising the steps of:
    (a) dissolving a glucosamine base having a purity level of at least 99.0 wt. % and a maximum halide content of about 0.01 wt. %, in water;
    (b) adding one or more pharmaceutically acceptable polymers to the aqueous glucosamine base solution resulting from step (a); and
    (c) recovering the stabilized glucosamine base composition from the reaction mixture produced in step (b).

9. The method of claim 8 wherein the polymer is employed in step (b) in an amount of about 2 to about 70 parts by weight, per part of the base.

10. The method of claim 8 wherein the polymer employed in step (b) comprises a water-soluble, water-dispersible and/or a water-swellable homopolymer and/or copolymer.

11. The method of claim 8 wherein the polymer is selected from the group consisting of carboxypolymethylene homopolymers and copolymers; polyethylene glycol homopolymers and copolymers; polypropylene glycol homopolymers and copolymers; ethylcellulose, povidone homopolymers and copolymers; polyacrylic acid homopolymers and copolymers; polyacrylamide homopolymers and copolymers; polysaccharides; and mixtures of two or more of the foregoing polymers.

12. The method of claim 8 wherein step (c) is carried out by adding a water-miscible solvent to the reaction mixture so as to precipitate the stabilized glucosamine base composition therefrom.

13. The method of claim 12 wherein the solvent comprises acetone.

14. The method of claim 8 wherein step (c) is carried out by freeze-drying.

15. The method of claim 14 wherein the freeze-drying is carried out at a pressure of not greater than about 500 milli-Torre and at a temperature of about −60 to about −20° C.

\* \* \* \* \*